United States Patent
Glaesemann

(10) Patent No.: US 7,461,564 B2
(45) Date of Patent: Dec. 9, 2008

(54) METHOD AND APPARATUS FOR PROOF TESTING A SHEET OF BRITTLE MATERIAL

(75) Inventor: Gregory Scott Glaesemann, Corning, NY (US)

(73) Assignee: Corning Incorporated, Corning, NY (US)

( * ) Notice: Subject to any disclaimer, the term of this patent is extended or adjusted under 35 U.S.C. 154(b) by 6 days.

(21) Appl. No.: 11/888,202

(22) Filed: Jul. 31, 2007

(65) Prior Publication Data

US 2008/0083288 A1    Apr. 10, 2008

Related U.S. Application Data

(60) Provisional application No. 60/849,298, filed on Oct. 4, 2006.

(51) Int. Cl.
*G01L 1/00* (2006.01)
(52) U.S. Cl. ................................. 73/862.381
(58) Field of Classification Search ............ 73/862.381, 73/831, 862.382; 65/378
See application file for complete search history.

(56) References Cited

U.S. PATENT DOCUMENTS

| | | | |
|---|---|---|---|
| 3,574,030 A | 4/1971 | Callander et al. | |
| 3,634,930 A | 1/1972 | Cranston | 29/574 |
| 4,019,365 A | 4/1977 | Woo | 73/15.6 |
| 4,148,218 A | 4/1979 | Knowles et al. | 73/829 |
| 4,302,978 A | 12/1981 | Dykmans | 73/828 |
| 4,302,979 A | 12/1981 | Dykmans | 73/828 |
| 4,317,368 A | 3/1982 | McElroy | 73/587 |
| 4,346,601 A | 8/1982 | France | 73/829 |
| 4,601,208 A | 7/1986 | McKay et al. | 73/829 |
| 4,639,131 A | 1/1987 | Maan | 356/73.1 |
| 5,016,476 A | 5/1991 | Peterson et al. | 73/829 |
| 5,076,104 A | 12/1991 | Glaesemann et al. | 73/830 |
| 5,138,879 A | 8/1992 | Shofner et al. | 73/160 |
| 5,167,150 A | 12/1992 | Shofner et al. | 73/160 |
| 5,203,206 A | 4/1993 | Shofner et al. | 73/160 |
| 5,207,106 A | 5/1993 | Schwider et al. | 73/828 |
| 5,437,193 A | 8/1995 | Schleitweiler et al. | 73/830 |
| 6,070,472 A | 6/2000 | Kipping et al. | 73/829 |
| 6,119,527 A | 9/2000 | Suhir | 73/830 |
| 6,527,120 B2 | 3/2003 | Okamoto | 206/454 |
| 6,834,553 B2 | 12/2004 | Ravichandran et al. | 73/829 |
| 6,863,747 B2 * | 3/2005 | Kashiwazaki et al. | 148/439 |
| 6,949,880 B1 | 9/2005 | Guenther et al. | 313/512 |
| 2001/0015256 A1 | 8/2001 | Yamazaki et al. | 156/289 |
| 2002/0069675 A1* | 6/2002 | Bumgarner et al. | 65/378 |
| 2003/0197197 A1 | 10/2003 | Brown et al. | 257/200 |
| 2004/0008179 A1 | 1/2004 | Chung et al. | 345/107 |
| 2004/0212599 A1 | 10/2004 | Cok et al. | 345/173 |
| 2004/0218133 A1 | 11/2004 | Park et al. | 349/153 |
| 2004/0224598 A1 | 11/2004 | Tanaka | 445/24 |
| 2004/0233156 A1 | 11/2004 | Yokota et al. | 345/104 |

(Continued)

*Primary Examiner*—Jewel Thompson
(74) *Attorney, Agent, or Firm*—Kevin M. Able

(57) ABSTRACT

Disclosed is a method of proof testing a sheet of brittle material such as a glass or glass-ceramic based material. The method comprises bending the glass sheet over at least one arcuate member to detect sheets having a strength greater than a predetermined value. The method includes imparting a bend to the sheet and producing relative motion between the sheet and the bend such that the bend traverses the sheet, and wherein tensile stress induced in a surface of the sheet by the bend corresponds to the predetermined strength value. An apparatus for performing the proof testing is also disclosed.

20 Claims, 4 Drawing Sheets

U.S. PATENT DOCUMENTS

| | | | |
|---|---|---|---|
| 2005/0170551 A1 | 8/2005 | Strip | 439/88 |
| 2005/0170735 A1 | 8/2005 | Strip | 445/24 |
| 2005/0214963 A1 | 9/2005 | Daniels et al. | 438/29 |

* cited by examiner

METHOD AND APPARATUS FOR PROOF TESTING A SHEET OF BRITTLE MATERIAL

This application claims the benefit of priority under 35 U.S.C. § 119(e) of U.S. Provisional Application Ser. No. 60/849,298 filed on Oct. 4, 2006.

BACKGROUND OF THE INVENTION

1. Field of the Invention

The present invention is directed to a method and apparatus for proof testing a brittle material, and in particular proof testing a glass or glass ceramic sheet.

2. Description of Related Art

Display devices utilizing plasma, liquid crystal, or organic light emitting diode display elements, to name a few, are fast overcoming cathode ray tube (CRT) displays in commercial products, finding use in a myriad of applications, from cell phones to televisions. However, the introduction of very thin, flexible displays is only in its infancy. This is due in no small part to the tremendous structural demands placed on such display devices: they must be capable of withstanding repeated flexing or bending without harm to the device or the substrate on which it is disposed; due to the intended use of flexible displays in portable devices, they are expected to withstand rough handling, again without undue harm to the device or substrate, and; they should be capable of withstanding a bending radius that can be less than 2 cm, and less than 1 cm in some cases.

One material contemplated for use in flexible displays is glass. Glass is generally chemically resistant, transparent, can form a hermetic barrier or seal, and may be formed into very thin sheets. Sheets in excess of 10 m$^2$ having thicknesses less than 1 mm, and even less than 0.7 mm have been produced and routinely used, and glass sheets are soon expected to reach dimension of at least about 100 m$^2$. In a typical display manufacturing process, multiple displays are formed using one or more large glass sheets or substrates. The displays are then separated into individual display units, usually by scoring and breaking. Thus, very large glass sheets are efficiently utilized by producing as many display units as possible.

Cutting glass, and in this case glass sheets, generally forms flaws (e.g. cracks) in the edges of the glass sheets. These flaws can serve as fracture sources, and thereby reduce the strength of the sheets, particularly if the glass is flexed such that the flaw experiences tensile stress. Generally, typical display devices do not experience significant flexing, thus the existence of these flaws is of less concern.

Flexible displays, by the very nature of their flexibility, may produce significant stress in the display substrate(s), either during the manufacturing process or in use. Thus, flaws that might be present in the glass may experience stresses sufficiently great that the glass will crack. Since typical display manufacturing involves cutting the glass to form individual displays, and cutting is known to create multiple flaws in the glass along the cut edge, this bodes poorly for the fate of glass substrate-based flexible display devices.

Attempts to mitigate flaws at the edges of glass sheets have included laser cutting, grinding, polishing and so forth, all in the attempt to remove or minimize the flaws that are created when the glass sheet is cut to size. However, many of these approaches are unsatisfactory for flexible display application, either because the technique is incapable of removing flaws down to the size needed for the expected stresses, or the technique is difficult to apply to such thin glass sheets (less than about 0.4 mm thick). Acid etching of the glass edges may be used, but may also degrade the display device disposed on the substrate. Thus, it would appear that regardless the method of cutting used, flaws will continue to be formed in glass sheets, and in particular at the edges of the sheet.

SUMMARY OF THE INVENTION

In one embodiment of the present invention a method of proof testing a sheet of brittle material is disclosed comprising imparting a bend to the sheet and producing relative motion between the sheet and the bend such that the bend traverses the sheet, and wherein tensile stress induced in a surface of the sheet by the bend corresponds to a predetermined strength value to detect sheets having a strength greater than the predetermined strength value.

In another embodiment, a method of proof testing a glass sheet is described comprising bending the glass sheet over at least one roller to bend the sheet and produce a tensile stress in a surface of the sheet that corresponds to a predetermined strength value, and producing relative motion between the sheet and the at least one roller such that successive portions of the sheet are subjected to the tensile stress to detect sheets having a strength greater than the predetermined strength value.

In still another embodiment, an apparatus for proof testing a sheet of brittle material is disclosed comprising at least one arcuate member for contacting the sheet and inducing a bend in the sheet of brittle material wherein a radius of curvature of the at least one arcuate member is selected such that a tensile stress induced in a surface of the sheet by the bending corresponds to a predetermined strength value to detect sheets having a strength greater than the predetermined value.

It is to be understood that both the foregoing general description and the following detailed description are merely exemplary of the invention, and are intended to provide an overview or framework for understanding the nature and character of the invention as it is claimed.

The accompanying drawings are included to provide a further understanding of the invention, and are incorporated in and constitute a part of this specification. The drawings are not necessarily to scale, and sizes of various elements may be distorted for clarity. The drawings illustrate one or more embodiment(s) of the invention, and together with the description serve to explain the principles and operation of the invention.

DETAILED DESCRIPTION

Figure 1:
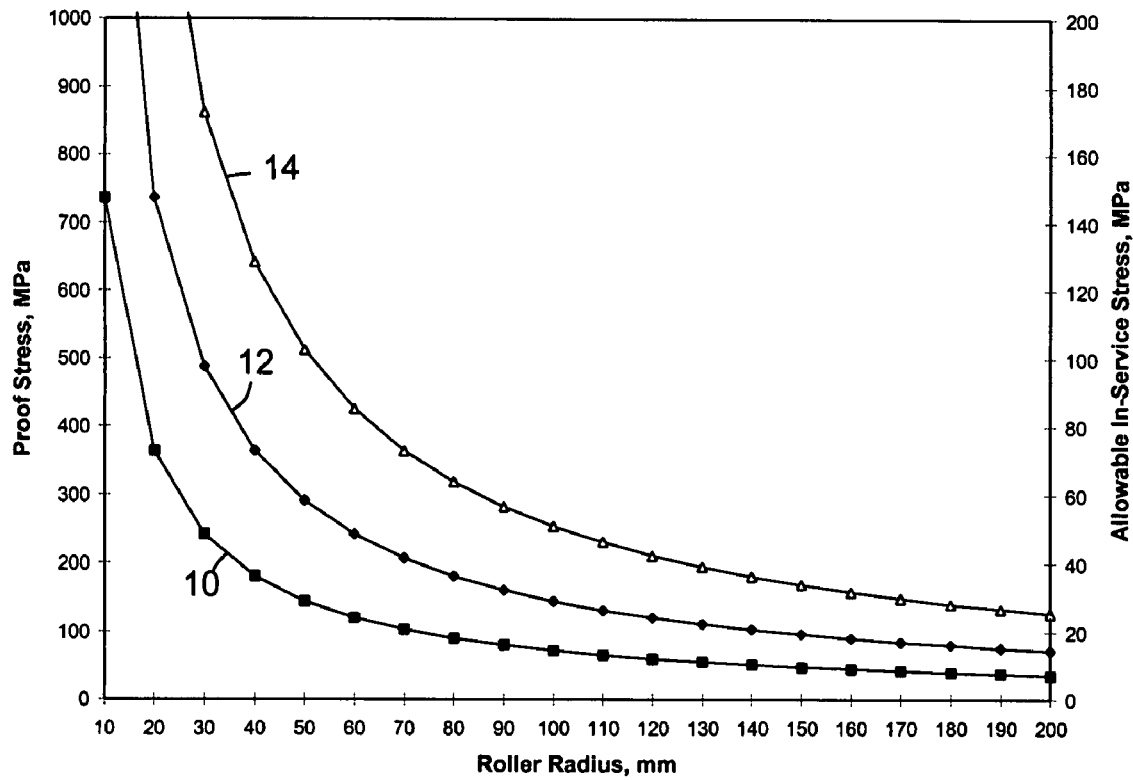
FIG. 1 is a plot of the tensile "proof test" stress in MPa applied as a function of the radius of curvature in cm of the arcuate member (e.g. roller) over which three thicknesses of glass sheet is bent.

The strength of glass is dictated by the presence of flaws in the glass. If tensile stress is applied to glass having a flaw, the stress becomes concentrated at the flaw. A flaw may be a microscopic crack for example, in which case the stress is concentrated at the tip of the crack. If the stress exceeds a certain magnitude, the original flaw—the crack—may grow. If sufficient stress is applied, crack growth may be virtually instantaneous, leading to catastrophic failure of the glass: it breaks.

Analogous to the strength of a chain being based on the strength of the weakest link, the strength of glass may be characterized as the strength of the largest, and therefore weakest, flaw. For example, if a tensile stress of 10 kpsi is applied to a glass fiber, and the fiber holds firm, the fiber is said to have a strength of at least 10 kpsi. That is, all the flaws that may exist on the glass fiber are smaller than that for which 10 kpsi would cause failure. As such, the "size" of a flaw in glass is often represented by stating the minimum tensile stress needed to cause catastrophic failure originating from that flaw. Thus, a glass fiber which has been stressed to 10 kpsi without breaking may be said to have no flaws "larger" than 10 kpsi. While a bit of a misnomer, the characterization of flaw size in terms of stress is common in the art of glass strength.

As can be appreciated by the preceding discussion, the strength of glass is a consequence of the history of the glass. That is, newly-formed glass is inherently exceptionally strong. As-drawn glass sheets can approach the strength of newly-formed glass fibers, typically in excess of 700 MPa. However, subsequent handling or exposure to environmental factors can create flaws, or enlarge existing flaws, thereby weakening the glass. For this reason, newly drawn optical fibers, for example, are immediately coated with a polymer coating to protect the surface of the glass and prevent, or at least minimize, a degradation in strength.

Glass sheets are commonly cut to size. For example, in a fusion glass sheet making process, molten glass is flowed over inclined forming surfaces on both sides of a wedge-shaped forming body. The two separate flows of glass converge at the bottom, or root, of the forming body where the inclined forming surfaces meet to produce a glass ribbon having pristine surfaces. The ribbon is subsequently cut into sheets of pre-determined length, typically by mechanical scoring. Later, the side edges of the sheet are also removed by a similar mechanical scoring process. Thus, edges of the sheet are subjected to forces that may damage the edges. This damage may, for example, comprise chipping or cracking of the sheet edge, resulting in diminished strength. The present invention addresses this issue by testing the glass sheet to detect the presence of flaws in the sheet, and particularly the edges of the sheet, that exceed a minimum size.

As described supra, brittle materials (e.g. glass) break in tension. One method of creating tension in glass is to bend the glass. For a given bend radius, the induced stress can be determined by the following equation:

$$\rho_p = E_0 \left(\frac{t}{2R}\right)\left[1 + \alpha \frac{t}{2R}\right] \quad \text{Eq. 1}$$

where t is the thickness of the sheet and R is the radius of the bend, $E_0$ is the zero stress Young's modulus of the material and a is the linear dependence of Young's modulus on strain that some brittle materials experience. FIG. 1 shows the calculated proof stress for sheets of Corning code 1737 glass where $E_0$ is about 70.9 GPa. The parameter α was chosen for pure silica, as a is unknown for code 1737 glass. Practically, however, α has only a 3% effect at 1% strain (100 kpsi), and may be omitted for simplicity without undue error occurring. The thicknesses of the sheets were 200 μm (curve 10), 400 μm (curve 12) and 700 μm (curve 14).

Figure 2:
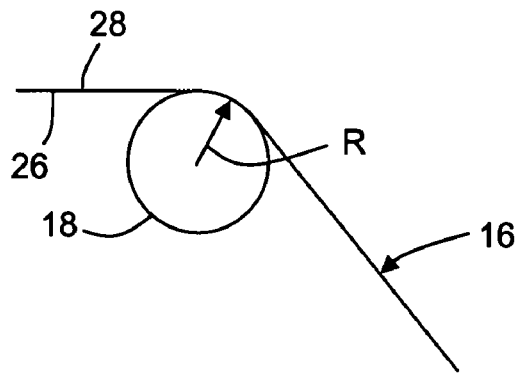
FIG. 2 is a side view of an apparatus for proof testing a sheet of brittle material according to an embodiment of the present invention utilizing a single roller or bushing.
Figure 3:
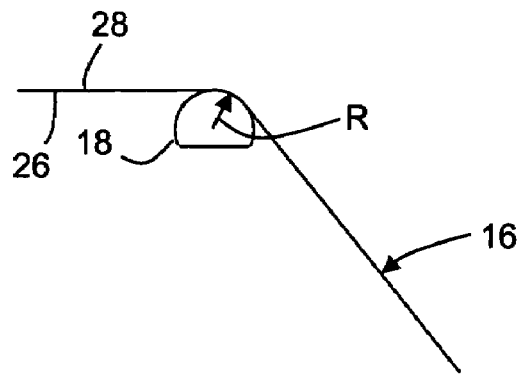
FIG. 3 is a side view of an apparatus for proof testing a sheet of brittle material according to an embodiment of the present invention utilizing a single non-circular arcuate member.

In accordance with an embodiment of the present invention, a method of proof testing a sheet of brittle material is described. The sheet of brittle material most commonly comprises glass or a glass ceramic, but may comprise other brittle materials that can be formed into flexible sheets. Referring to FIG. 2, in its simplest embodiment the present invention can be represented by bending the sheet of brittle material 16 over arcuate member 18 having a radius of curvature R that imparts a bend to the sheet. Arcuate member 18 may be a rotatably mounted roller, as shown in FIG. 2, but may also be a fixed bushing (e.g. non-rotating), or, as shown in FIG. 3, may be simply a form with an arcuate surface formed from a material having a low coefficient of friction (e.g. a fluoropolymer resin such as DuPont Teflon®). Sheet 16 may be moved over arcuate member 18 such that a pre-determined length of sheet 16 is sequentially subjected to the imposed bend radius. The pre-determined length may be the entire length, or a sub-length of the sheet. Alternatively, the arcuate member may be moved over sheet 16 and arcuate member maintained stationary.

Figure 4:
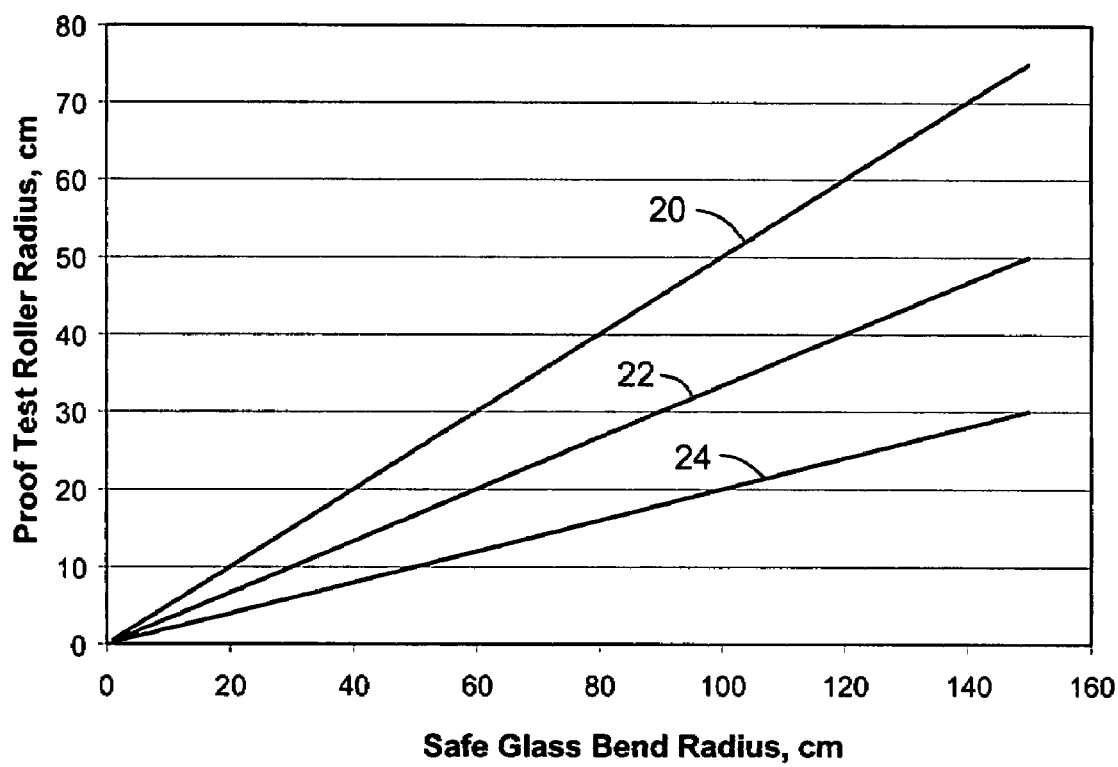
FIG. 4 is a plot showing the "safe" stress that can be applied to a glass sheet that has been proof tested in accordance with the present invention as a function of the bend radius used in the proof testing.

The radius of curvature R of the arcuate member is selected such that it imparts the desired stress to the sheet, such as per equation 1 above. That is, the desired stress level, and hence the desired minimum strength, may be determined by the radius of curvature of the arcuate member over which the sheet is bent. FIG. 4 depicts the radius of curvature necessary during proof testing of the sheet to provide a subsequent "safe" bend radius for subsequent use, e.g. during transient bending conditions (curve 20); during longer term bending (hours of bending—curve 22), and; bending conditions which span years (e.g. greater than 5 years—curve 24). For example, looking at FIG. 4, a proof testing bend radius of 50 cm (the radius of curvature of the arcuate member) would be needed to ensure a service life longer than 5 years if the sheet comprises a persistent bend radius of 100 cm. Such conditions might be encountered if the sheet were rolled for storage for a prolonged time.

As should be apparent from the preceding description, the use of a single arcuate member necessarily entails a change in direction for the sheet (assuming movement of the sheet over the arcuate member). Perhaps more importantly, the embodiments of FIGS. 2 and 3 result in a tensile stress being applied to only a single side of sheet 16. That is, bending in only a single direction places the side opposite the arcuate member in tension, while the side in contact with the arcuate member is in compression. To subject the opposite side of sheet 16 to the same tensile stress as the first side, it would be necessary to flip the sheet and proceed to run the length of sheet over the arcuate member a second time.

Figure 5:
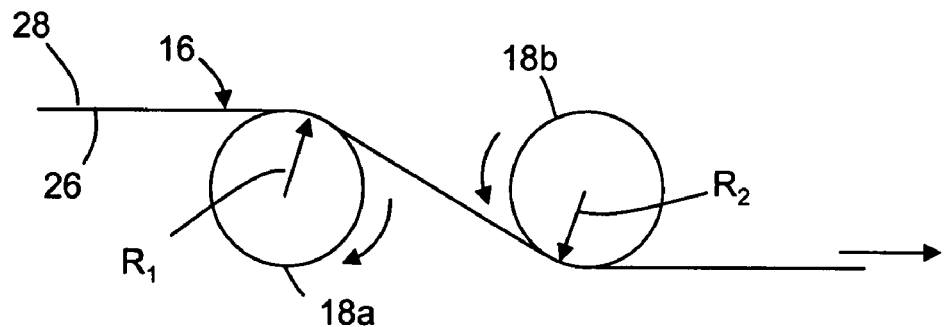
FIG. 5 is another embodiment of the present invention utilizing two arcuate members for bending the sheet of brittle material in different directions.

A more efficient embodiment of the present invention is illustrated in FIG. 5 wherein two arcuate members are in contact with sheet 16. Each of the two arcuate members 18a and 18b contact sheet 16 on an opposite side from the other arcuate member. That is, the arcuate members alternate sides in contacting the sheet. Sheet 16 is bent over the first arcuate member 18a having radius of curvature $R_1$ in one direction (e.g. in a clockwise direction, then bent over the second arcuate member 18b having second radius of curvature $R_2$ in a second direction (e.g. counter-clockwise) different from the first direction. Thus, a first side 26 of sheet 16 is subjected to a tensile stress, then the second side 28 is subjected to a tensile stress, requiring only a single pass of sheet 16 between the arcuate members to apply a tensile stress to both sides of the sheet. To ensure the edges of the sheet are protected from mechanical damage after proof testing, the edges may be coated with a protective coating. For example, the edges may be coated with a polymer coating layer. In some embodiments, the entire sheet may be coated on one or both sides.

Figure 6:
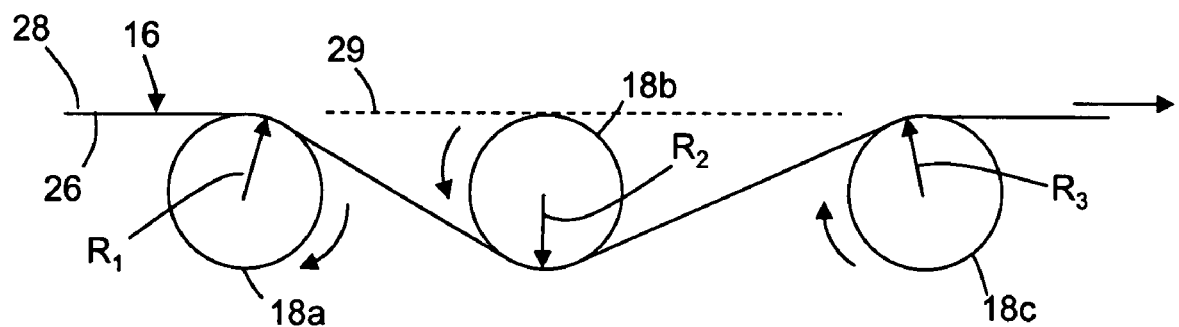
FIG. 6 is another embodiment of the present invention utilizing three arcuate members for bending the sheet of brittle material in different directions and returning the sheet to the entry plane.

It should be readily apparent that additional rollers may also be used. For example, if it is desired to remove the sheet from between the arcuate members in the same plane 29 in which the sheet enters the arcuate members, third arcuate member 18c having radius of curvature $R_3$ may be added as depicted in FIG. 6. Such conditions may be imposed by physical space considerations, for example. $R_1$, $R_2$ and $R_3$ are preferably equal (the same), but may be different if desired.

Figure 7:
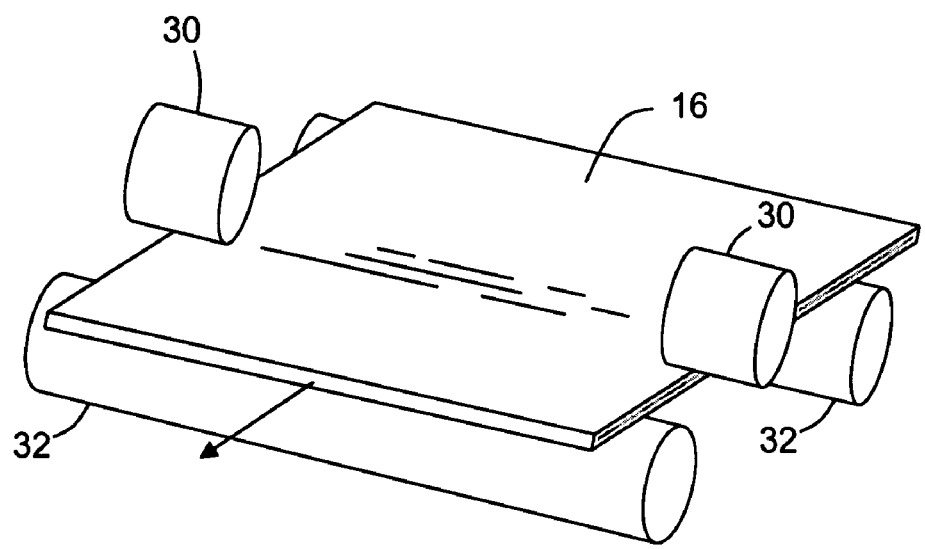
FIG. 7 is another embodiment of the present invention utilizing arcuate members which contact only the edges of the sheet of brittle material on one side of the sheet, and arcuate members which contact the sheet across the entire width of the sheet on the other side.
Figure 8:
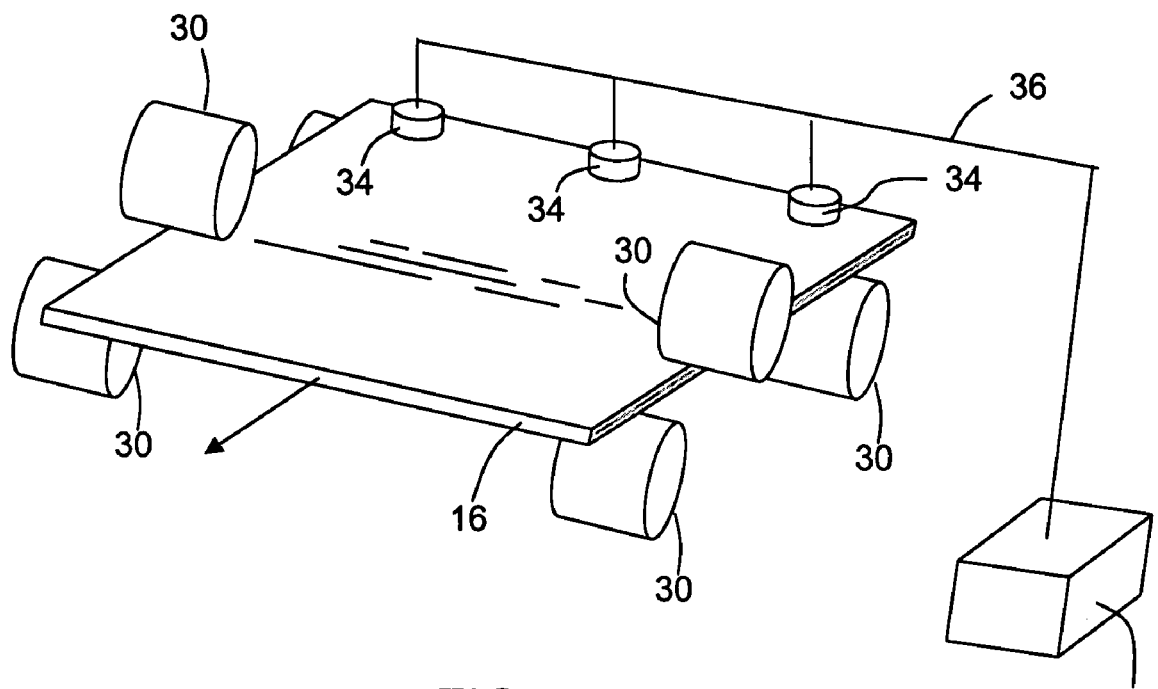
FIG. 8 is another embodiment of the present invention utilizing arcuate members which contact only the edges of the sheet of brittle material.

The preceding embodiments employed an arcuate member that spanned the entire width of the sheet. In some embodiments, it may be undesirable to contact the entire width. For example, glass sheets used in the manufacture of flat panel displays must meet stringent surface quality requirements. Contacting the serviceable or "quality" areas of the sheet may impart surface defects that make the sheet unusable. Generally, the quality area is defined as the area inboard of any area contacted during processing. Consequently, the arcuate member may be adapted such that only the peripheral regions of the sheet are contacted by the arcuate member on at least one side of the sheet, proximate the outer edges of the sheet. Such a configuration is shown in FIG. 7, where glass sheet 16 is illustrated passing between edge rollers 30 on one side, and full-width rollers 32 on the opposite side. Sheet 16 is moving in a direction indicated by the directional arrow in the figure. This arrangement preserves the surface quality on at least one side of the sheet. If contact with both sides of the sheet should be minimized, edge rollers may be used to contact the sheet at the peripheral portions of the sheet on both sides of the sheet without contacting the quality areas of the sheet on either side. FIG. 8 is similar to the situation shown in FIG. 7, but depicts edge rollers 30 contacting both side edges of sheet 16 without contacting the central quality area 32 on either side of the sheet.

In the event that a flaw having a strength less than the tensile stress applied by bending the sheet, the sheet may fracture. In some embodiments, particularly if the glass is uncoated, the fracture may be self-evident: the sheet breaks into two or more separate pieces. In other embodiments, the sheet may be coated, such as with a polymer film on one or both sides of the sheet. In such cases, fracture may not be immediately detected, particularly in an automated manufacturing process. Thus, audio detection methods can be effectively used to detect fracture. For example, sheet 16 may be fed between bend-inducing rollers 32 on a transport line, with acoustic sensors 34 placed close to a surface of the sheet. A fracture in the sheet produces a sound that is detected by the acoustic sensors. The acoustic sensors are electrically coupled through control line 36 to control device 38 (e.g. computer 38) that may, for example, be adapted to stop movement of the sheet between the rollers. Other control functions may also be included, such as activating an audible and/or visual alarm.

It will be apparent to one skilled in the art given the benefit of the present disclosure that the various roller configurations described herein may be mounted on a stationary frame wherein the sheet of brittle material moves relative to the rollers such that successive portions of the sheet are strength tested. Alternatively, small rollers may be mounted on a hand-held frame to produce a portable, hand-held strength tester. An edge of the sheet of brittle material to be tested is then placed between the rollers of the hand-held strength tester and an operator holding the tester translates the tester relative to the sheet, testing the strength of one edge of the sheet at a time relative to a pre-determined strength value.

While the invention has been described in conjunction with specific exemplary embodiments thereof, it is evident that many alternatives, modifications, and variations will be apparent to those skilled in the art in light of the foregoing description. Accordingly, the present invention is intended to embrace all such alternatives, modifications, and variations as fall within the spirit and broad scope of the appended claims.

What is claimed is:

1. A method of proof testing a sheet of brittle material comprising imparting a bend to the sheet and producing relative motion between the sheet and the bend such that the bend traverses the sheet, and wherein tensile stress induced in a surface of the sheet by the bend corresponds to a predetermined strength value to detect sheets having a strength greater than the predetermined strength value.

2. The method according to claim 1 wherein imparting the bend comprises bending the sheet over an arcuate member.

3. The method according to claim 1 further comprising bending the sheet over a plurality of arcuate members to impart a plurality of bends, the plurality of arcuate members contacting the sheet on alternating sides of the sheet.

4. The method according to claim 2 wherein the arcuate member is a roller.

5. The method according to claim 3 wherein the plurality of arcuate members comprises a plurality of rollers.

6. The method according to claim 2 wherein the arcuate member does not contact a center portion of the sheet.

7. The method according to claim 2 wherein the arcuate member extends across an entire width of the sheet.

8. The method according to claim 1 wherein the sheet of brittle material comprises a glass or a glass ceramic.

9. The method according to claim 1 wherein a break in the sheet is detected with an acoustic sensor.

10. The method according to claim 1 wherein a radius of curvature of the arcuate member is less than about 20 cm.

11. The method according to claim 1 wherein the sheet is coated with a polymer layer.

12. A method of proof testing a glass sheet comprising bending the glass sheet over at least one roller to bend the sheet and produce a tensile stress in a surface of the sheet that corresponds to a predetermined strength value, and producing relative motion between the sheet and the at least one roller such that successive portions of the sheet are subjected to the tensile stress to detect sheets having a strength greater than the predetermined strength value.

13. The method according to claim 12 wherein the glass sheet has a thickness less than about 0.4 mm.

14. The method according to claim 12 wherein the tensile stress is at least about 50 MPa.

15. The method according to claim 12 wherein the at least one roller comprises a plurality of rollers contacting alternating sides of the glass sheet.

16. An apparatus for proof testing a sheet of brittle material comprising at least one arcuate member for contacting the sheet and inducing a bend in the sheet of brittle material wherein a radius of curvature of the at least one arcuate member is selected such that a tensile stress in a surface of the sheet induced by the bending corresponds to a predetermined strength value to detect sheets having a strength greater than the predetermined value.

17. The apparatus according to claim 16 wherein the arcuate member is a roller.

18. The apparatus according to claim 16 wherein the at least one arcuate member comprises a plurality of arcuate members.

19. The apparatus according to claim 18 wherein the plurality of arcuate members are a plurality of rollers.

20. The apparatus according to claim 18 wherein the plurality of arcuate members do not contact a center portion of the sheet.

* * * * *